US006388117B2

(12) United States Patent
Pinske

(10) Patent No.: US 6,388,117 B2
(45) Date of Patent: *May 14, 2002

(54) PROCESS FOR PREPARING CARBAMATOORGANOSILANES AND ISOCYANATOORGANOSILANES

(75) Inventor: Klaus Pinske, Haltern (DE)

(73) Assignee: Degussa AG, Duesseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/460,762

(22) Filed: Dec. 14, 1999

(30) Foreign Application Priority Data

Dec. 14, 1998 (DE) .......................... 198 57 532

(51) Int. Cl.⁷ ................ C07F 7/02; C07F 7/04
(52) U.S. Cl. ............ 556/411; 556/412; 556/420; 556/421

(58) Field of Search ................... 556/411, 414, 556/420, 421, 412

(56) References Cited

U.S. PATENT DOCUMENTS

| | | | | | |
|---|---|---|---|---|---|
| 3,702,860 A | * | 11/1972 | Krahnke et al. | ............ | 556/411 |
| 4,046,794 A | * | 9/1977 | Pepe et al. | ................... | 556/414 |
| 4,386,033 A | * | 5/1983 | Konig et al. | ................... | 560/24 |
| 4,480,110 A | * | 10/1984 | Heitkamper et al. | ........... | 560/24 |
| 5,393,910 A | * | 2/1995 | Mui et al. | ................... | 556/414 |

* cited by examiner

Primary Examiner—Richard L. Raymond
Assistant Examiner—Venkataraman Balasubramanian
(74) Attorney, Agent, or Firm—Oblon, Spivak, McClelland, Maier & Neustadt, P.C.

(57) ABSTRACT

Processes for preparing carbamatoorganosilanes from aminoorganosilanes, ureas and alcohols. These compounds are useful for surface modification of inorganic and organic materials, as adhesion promoters between inorganic materials and organic polymers, as crosslinking agents for the moisture-curing of polymers, for PU sealants, in the coating and adhesive sector, and for the production of biologically active products, such as insecticides and herbicides.

21 Claims, No Drawings

PROCESS FOR PREPARING CARBAMATOORGANOSILANES AND ISOCYANATOORGANOSILANES

BACKGROUND OF THE INVENTION

1. Field of the Invention

The present invention relates to a process for preparing carbamatoorganosilanes from aminoorganosilanes, urea and alcohols. The present invention relates, in particular, to a process for the thermal catalyzed cleavage of carbamatoorganosilanes to form isocyanatoorganosilanes.

2. Background of the Invention

Processes for preparing carbamatoorganosilanes and isocyanatoorganosilanes are known. For example, carbamatoorganosilanes are prepared by reacting aminoorganosilanes with phosgene in the presence of tertiary amines (see DE-A 35 44 601, JP-A-4 223 171). In addition to the phosgene toxicity and the resulting safety precautions, the formation of chlorine-containing by-products and the unavoidable production of salts are disadvantageous. In addition, certain carbamatoorganosilane compounds cannot be prepared, owing to the reaction conditions.

In other processes, instead of phosgene, use of made of haloformates in the presence of tertiary amines or halosilanes (see JP-A-63 250 391, JP-A-01 275 587), or carbon dioxide in the presence of tertiary amines and halosilanes (see CA 1 108 174, DE-A 27 22 117), or organic carbonates catalyzed by strong bases (see EP-A 0 583 581). The disadvantages of these processes are, in addition to some low yields, the formation of halogen-containing by-products and salts.

Processes for preparing isocyanatoorganosilanes are the hydrosilylation of alkene isocyanates in the presence of differing noble metal catalysts at elevated temperature (see EP-A 0 709 392, JP-A-5 206 525, U.S. Pat. No. 1,371,405). The processes are disadvantageous in some cases in that low selectivities, by-product formation and the higher catalyst concentrations required, which in addition to the cost factor leads to contamination and waste problems.

In addition, processes are known according where haloorganosilanes react with metal cyanates to form isocyanuratosilanes or, in the presence of alcohols, to form carbamatoorganosilanes which cleave thermally to form isocyanatoorganosilanes (see U.S. Pat. No. 3,821,218, U.S. Pat. No. 3,598,852, U.S. Pat. No. 3,494,951, CA 943 544, DE-A 35 24 215). The high reaction temperatures and the production of salts are disadvantageous. The solvent preferably used is dimethylformamide, which is toxic.

The thermal cleavage of carbamatoorganosilanes under atmospheric or reduced pressure in the gas or liquid phase is likewise a process for preparing isocyanatoorganosilanes (see U.S. Pat. No. 5,393,910, JP-A-63 250 391, U.S. Pat. No. 3,607,901, EP-A 0 649 850). Although the cleavage outputs are increased by higher temperatures where necessary and addition of halosilane compounds on occasion, the formation of by-products increases simultaneously. Continuous processes for preparing aliphatic and cycloaliphatic biscarbamates from urea, diamines and alcohols and the catalytic cleavage of the biscarbamates in the liquid phase to form diisocyanates are known (see EP-A 0 355 443, EP-A 0 568 782).

SUMMARY OF THE INVENTION

It is an object of the present invention to provide improved, economic processes for preparing carbamatoorganosilanes, ureoorganosilanes and isocyanatoorganosilanes avoiding the disadvantages discussed above.

It is another object to provide continuous processes for preparing carbamatoorganosilanes, ureoorganosilanes and isocyanatoorganosilanes.

The objects of the invention, and others, may be accomplished with a process for preparing a carbamatoorganosilane represented by formula (V):

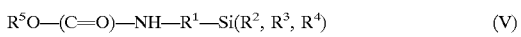
$$R^5O-(C=O)-NH-R^1-Si(R^2, R^3, R^4) \quad (V)$$

where $R^1$ is an alkyl, branched alkyl, cycloalkyl, alkenyl, alkylalkoxyalkyl, aryl, alkaryl, or aralkyl group;

$R^2$, $R^3$, $R^4$ are each, independently, an alkyl, branched alkyl, cycloalkyl, alkoxy, alkoxy-substituted alkoxy, siloxy, aryl, alkaryl, or aralkyl group;

$R^5$ is an alkyl, branched alkyl, cycloalkyl, aryl, alkaryl, or aralkyl group;

where $R^1$, $R^2$, $R^3$, and $R^4$ may each be, independently, substituted with one or more functional groups, comprising:

(a) reacting an aminoorganosilane represented by formula (I), a urea represented by formula (II) and an alcohol represented by formula (IV) in a stirred-tank cascade at 150–250° C. and 7–40 bar or (b) (i) reacting an aminoorganosilane represented by formula (I) and a urea represented by formula (II) in an alcohol solvent represented by formula (IV) in a distillation reactor at 100–130° C. and 0.7–1.5 bar (absolute) to form an ureoorganosilane represented by formula (III), followed by (ii) reacting the ureoorganosilane represented by formula (III) with an alcohol represented by formula (IV) in a pressure distillation reactor at 150–250° C. and 7–40 bar,

$$H_2N-R^1-Si(R^2, R^3, R^4) \quad (I)$$

$$H_2N-(C=O)-NH_2 \quad (II)$$

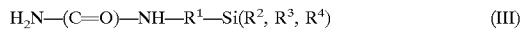
$$H_2N-(C=O)-NH-R^1-Si(R^2, R^3, R^4) \quad (III)$$

$$R^5-OH \quad (IV)$$

where $R^1$, $R^2$, $R^3$, $R^4$ and $R^5$ are as defined above.

The objects of the invention may also be accomplished with a process for preparing an ureoorganosilane represented by formula (III):

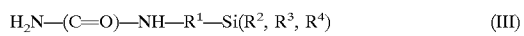
$$H_2N-(C=O)-NH-R^1-Si(R^2, R^3, R^4) \quad (III)$$

where $R^1$ is an alkyl, branched alkyl, cycloalkyl, alkenyl, alkylalkoxyalkyl, aryl, alkaryl, or aralkyl group; and $R^2$, $R^3$, $R^4$ are each, independently, an alkyl, branched alkyl, cycloalkyl, alkoxy, alkoxy-substituted alkoxy, siloxy, aryl, alkaryl, or aralkyl group;

where $R^1$, $R^2$, $R^3$, and $R^4$ may each be, independently, substituted with one or more functional groups, comprising:

reacting an aminoorganosilane represented by formula (I) and a urea represented by formula (II) in an alcohol solvent represented by formula (IV) in a distillation reactor at 100–130° C. and 0.7–1.5 bar (absolute), $$H_2N-R^1-Si(R^2, R^3, R^4) \quad (I)$$

$$H_2N-(C=O)-NH_2 \quad (II)$$

$$R^5-OH \quad (IV),$$

where

R$^1$, R$^2$, R$^3$, R$^4$ and R$^5$ are as defined above; and

R$^5$ is an alkyl, branched alkyl, cycloalkyl, aryl, alkaryl, or aralkyl group;

The objects of the invention may also be accomplished with a process for preparing an isocyanatoorganosilane represented by formula (VI):

$$OCN-R^1-Si(R^2, R^3, R^4) \quad (VI)$$

where

R$^1$ is an alkyl, branched alkyl, cycloalkyl, alkenyl, alkylalkoxyalkyl, aryl, alkaryl, or aralkyl group; and R$^2$, R$^3$, R$^4$ are each, independently, an alkyl, branched alkyl, cycloalkyl, alkoxy, alkoxy-substituted alkoxy, siloxy, aryl, alkaryl, or aralkyl group;

wherein R$^1$, R$^2$, R$^3$, and R$^4$ may each be, independently, substituted with one or more functional groups, comprising:

(a) reacting an aminoorganosilane represented by formula (I), a urea represented by formula (II) and an alcohol represented by formula (IV) in a stirred-tank cascade at 150–250° C. and 7–40 bar, or (b) (i) reacting an aminoorganosilane represented by formula (I) and a urea represented by formula (II) in an alcohol solvent represented by formula (IV) in a distillation reactor at 100–130° C. and 0.7–1.5 bar (absolute) to form an ureoorganosilane represented by formula (III), followed by (ii) reacting the ureoorganosilane represented by formula (III) with an alcohol represented by formula (IV) in a pressure distillation reactor at 150–250° C. and 7–40 bar to produce a carbamatoorganosilane represented by formula (V), and (c) catalytically cleaving the carbamatoorganosilane represented by formula (V) in the liquid phase, $$H_2N-R^1-Si(R^2, R^3, R^4) \quad (I)$$

$$H_2N-(C=O)-NH_2 \quad (II)$$

$$H_2N-(C=O)-NH-R^1-Si(R^2, R^3, R^4) \quad (III)$$

$$R^1-OH \quad (IV)$$

$$R^5O-(C=O)-NH-R^1-Si(R^2, R^3, R^4) \quad (V)$$

where

R$^1$, R$^2$, R$^3$, R$^4$ and R$^5$ are as defined above; and

R$^5$ is an alkyl, branched alkyl, cycloalkyl, aryl alkaryl, or aralkyl group;

A more complete appreciation of the invention and many of the attendant advantages thereof will be readily obtained as the same becomes better understood by reference to the following detailed description.

DETAILED DESCRIPTION OF THE INVENTION

The present invention provides:

(a) the single-stage preparation of carbamatoorganosilanes (V), (b) preferably the two-stage preparation of carbamatoorganosilanes (V), in a first step ureoorganosilanes (III) being formed from aminoorganosilanes (I), urea (II) and alcohols (IV), and (c) the catalytic cleavage of carbamatoorganosilanes (V) in the liquid phase to form isocyanatoorganosilanes (VI), according to the following reaction scheme:

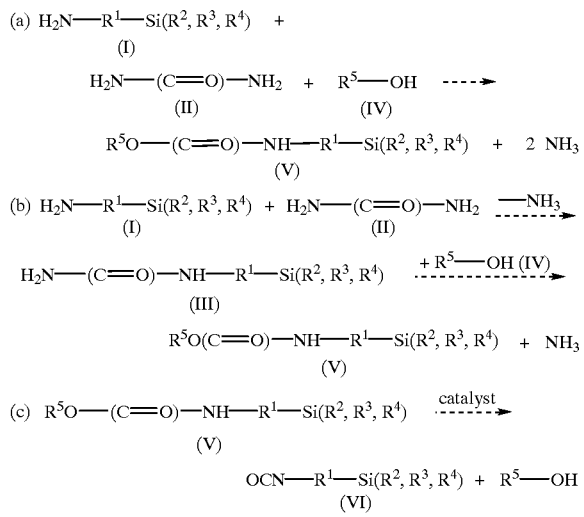

where

R$^1$=alkyl, branched alkyl, cycloalkyl, alkenyl, alkylalkoxyalkyl, aryl, alkaryl, aralkyl group;

R$^2$, R$^3$, R$^4$=alkyl, branched alkyl, cycloalkyl, alkoxy, alkoxy-substituted alkoxy, siloxy, aryl, alkaryl, aralkyl group;

R$^5$=alkyl, cycloalkyl group or in accordance with the groups R$^2$, R$^3$, R$^4$.

R$^1$, R$^2$, R$^3$, R$^4$, in addition, can contain functional group, such as ether, thioethers, sulfones, ketones, esters, amides, nitrile.

The present invention also provides process for preparing carbamatoorganosilanes (V) by (a) single-stage reaction of aminoorganosilanes (I), urea (II) and alcohols (IV) in a stirred-tank cascade at 150–250° C. and 7–40 bar or (b) two-stage reaction of aminoorganosilanes (I) and urea (II) in alcohols (IV) as solvent in a distillation reactor at 100–130° C. and 0.7–1.5 bar (absolute) to form ureoorganosilanes (III) as intermediate and the subsequent reaction of (III) with alcohols (IV) in a pressure distillation reactor at 150–250° C. and 7–40 bar.

According to the invention, the preparation by single-stage reaction can lead directly to the end product (V). However, preferably, (V) is prepared according to the invention by a two-stage preparation, in particular continuously, the intermediate (III) being prepared in a first step. This intermediate can be isolated or further reacted directly to form (V).

The invention therefore also relates to a process for preparing ureoorganosilanes (III) by reaction of aminoorganosilanes (I) and urea (II) in alcohols (IV) as solvents in a distillation reactor at 100–130° C. and 0.7–1.5 bar (absolute).

The invention further relates to a process for preparing isocyanatoorganosilanes (VI) by (a) single-stage reaction of aminoorganosilanes (I), urea (II) and alcohols (IV) in a stirred-tank cascade at 150–250° C. and 7–40 bar, or (b) two-stage reaction of aminoorganosilanes (I) and urea (II) in alcohols (IV) as solvent in a distillation reactor at 100–130° C. and 0.7–1.5 bar (absolute) to form ureoorganosilanes (III) as intermediate and subsequent reaction of (III) with alcohols (IV) in a pressure distillation reactor at 150–250° C. and 7–40 bar to give carbamatoorganosilanes (V), and (c) catalytic cleavage of (V) in the liquid phase.

In one particular embodiment of the present invention, $R^1$, $R^2$, $R^3$, $R^4$ and $R^5$ may each, independently, have 1 to 20 carbon atoms, inclusive of all specific values and subranges there between, such as 2, 5, 8, 10, 12, 15 and 18 carbon atoms. Suitable examples include alkyl groups, of any structure, having from 1 to 8 carbon atoms. Phenyl is a preferred aryl group.

In another embodiment, $R^1$, $R^2$, $R^3$, and IV may, independently, be substituted with one or more functional groups. Such functional groups include ethers, thioethers, sulfones, ketones, esters, amides, nitriles. $R^1$, $R^2$, $R^3$, and $R^4$ may be substituted with, for example, one, two or three functional groups.

In another embodiment of the present invention, $R^5$ is an alkyl, branched alkyl, or cycloalkyl group.

In still another embodiment of the invention, the processes may be conducted continuously.

Examples of aminoorganosilanes (I) which may be used in the inventive process include:

gamma-aminopropyltrimethoxysilane
gamma-aminopropyltriethoxysilane
gamma-aminopropylmethyldiethoxysilane
gamma-aminopropylmethyldimethoxysilane
gamma-aminopropylethyldiethoxysilane
gamma-aminopropylphenyldiethoxysilane
gamma-aminopropylphenyldimethoxysilane
delta-aminobutyltrimethoxysilane
delta-aminobutyltriethoxysilane
delta-aminobutylmethyldiethoxysilane
delta-aminobutylmethyldimethoxysilane
delta-aminobutylethyldiethoxysilane
delta-aminobutylethyldimethoxysilane
delta-aminobutylphenyldiethoxysilane
delta-aminobutylphenyldimethoxysilane
beta-aminoisopropyltrimethoxysilane
beta-aminobutyltrimethoxysilane
beta-aminobutyltriethoxysilane
beta-aminobutylmethyldiethoxysilane
beta-aminobutylmethyldimethoxysilane
beta-aminobutylethyldiethoxysilane
beta-aminobutylethyldimethoxysilane
beta-aminobutylphenyldiethoxysilane
beta-aminobutylphenyldimethoxysilane
gamma-aminopropyltripropoxysilane
gamma-aminopropyltributoxysilane
gamma-aminopropylphenyhnethyl-n-propoxysilane
gamma-aminopropylmethyldibutoxysilane
gamma-aminopropyltris(methoxyethoxyethoxy)silane
gamma-aminopropyldimethylethoxysilane
gamma-aminopropyldiethylmethylsilane
gamma-aminopropyldiethylmethylsilane
gamma-aminopropyltris(timethylsiloxy)silane
ω-aminoundecyltrimethoxysilane
delta-aminobutyldimethylmethoxysilane
delta-amino(3-methylbutyl)methyldimethoxysilane
delta-amino(3-methylbutyl)methyldiethoxysilane
delta-amino(3-methylbutyl)trimethoxysilane, and preferably
gamma-aminopropyltimethoxysilane
gamma-aminopropyltriethoxysilane
gamma-aminopropylmethyldiethoxysilane and
gamma-aminopropylmethyldiethoxysilane.

Suitable alcohols (IV) include all primary alcohols which firstly have a sufficiently high difference in boiling temperature from the respective carbamatoorganosilane and secondly permit evaporation of the carbamatoorganosilane and condensation of the cleavage products under operating pressures which are expedient in terms of the process.

Furthermore, the alcohol should be selected in such a manner that no reactions, e.g. transesterifications, with the $Si(R^2, R^3, R^4)$ group occur. Therefore, particularly suitable alcohols are methanol, ethanol, propanol, butanol, isobutanol, pentanol, isopentanol, hexanol, isohexanol, cyclohexanol, 2-ethylhexanol, preferably methanol, and ethanol.

A description is given below of the preferred two-stage continuous preparation of carbamatoorganosilanes.

The abbreviations denote the following:

| | | |
|---|---|---|
| AOS: aminoorganosilane | | (I) |
| UOS: ureoorganosilane | | (III) |
| COS: carbamatoorganosilane | | (V) |
| IOS: isocyanatoorganosilane | | (VI) |

AOS is reacted with urea to form UOS in the presence of alcohol as solvent in a distillation reactor, the starting materials being continuously delivered to the uppermost plate and the ammonia released being expelled by alcohol vapors which are introduced in the bottom of the distillation reactor. The ammonia/alcohol mixture is, to prevent ammonium carbamate from depositing, partially condensed in a condenser at temperatures of from 20 to 50° C. From the condensate, ammonia-free alcohol is recovered by distillation in the column, for example downstream, of the pressure distillation reactor.

The molar ratio of the starting materials AOS:urea:alcohol varies from 1:1.0–1.2:3–10. The distillation reactor has at least 4 plates. The reaction is carried out at temperatures of from 100 to 130° C. and pressures of from 0.7 to 1.4 bar (absolute). The residence time required in the distillation reactor is from 4 to 10 h, preferably from 6 to 8 h. The amount of alcohol introduced in the bottom to expel the ammonia is from 0.05 to 3 kg/kg, preferably from 0.1 to 1 kg/kg of UOS, the amount of alcohol thus introduced being taken off at the top together with the ammonia formed, freed of residual ammonia after partial condensation in a alcohol recovery column and recycled to the bottom.

To achieve as complete as possible a conversion of the urea to UOS, without (N-unsubstituted) O-organocarbamatosilane already forming, the reaction temperature is preferably restricted to a maximum of 130° C. The reaction rate given by the desired reaction temperature, and the type and ratio of starting materials determines the residence time and thus the dimensioning of the distillation reactor.

The advantage of the distillation reactor over a stirred-tank cascade (single stage) is that the reaction mixture in a distillation column is passed in countercurrent to the alcohol vapors introduced in the bottom, each plate virtually corresponding to a cascade stage. By means of the alcohol vapors introduced, the liquid is intensively mixed on the individual plates in such a manner that corresponding stirrer devices are no longer required. This results in a device which is expedient in terms of energy, operations and capital expenditure. The energy consumption is considerably lower than in the stirred-tank cascade, since the alcohol vapors need to be generated and condensed only once. The expenditure on apparatus and instrumentation is correspondingly low.

The crude UOS which is dissolved in alcohol and is produced in the bottom of the distillation reactor is continuously run, together with the circulating material, to the uppermost plate of the pressure distillation reactor. The feed can be brought to the required reaction temperature outside the column using a heat exchanger or alternatively in the column by an immersion heater or the like.

Here, UOS reacts with the alcohol to form COS at elevated temperature and elevated pressure, ammonia being released which, for kinetic reasons, must be removed from the reaction mixture. This is achieved by alcohol vapors which are introduced in the bottom of the pressure distillation reactor.

The alcohol vapors are expediently generated in an evaporator mounted at the bottom of the column.

The advantages of the pressure distillation reactor over a stirred-tank cascade are the same as for the distillation reactor. The stages required for complete conversion cannot be implemented for cost reasons when a stirred-tank cascade is used, so that incomplete reaction and thus corresponding loss of yield must be accepted for this (see also Ullmanns Encyklopädie der technischen Chemie [Ullmann's Encyclopedia of Industrial Chemistry], 4th edition 1973, Vol. 3, pp. 342–349), incorporated herein by reference.

The COS formation reaction rate is determined by the parameters temperature, pressure, ratio of UOS to alcohol, alcohol vapors introduced in the bottom and number of stages of the pressure distillation reactor. For the process according to the invention, pressures of from 7 to 40 bar, temperatures in the bottom of the pressure distillation reactor of from 150 to 250° C. and, at the top of the pressure distillation reactor, of from 130 to 210° C., a molar ratio of biurea to alcohol of from 1:2 to 12, alcohol vapors introduced in the bottom in the amount of from 0.5 to 8 kg/kg, preferably from 1 to 4 kg/kg of COS formed have proved to be expedient. The mean residence time in the pressure distillation reactor required for complete conversion is from 5 to 20 h, preferably from 8 to 14 h.

Owing to the low reaction rate of the reaction of COS with alcohol, a high temperature is desirable, but because of the formation of by-products, is restricted to a maximum of 250° C. The column pressure establishes itself accordingly and then is only dependent on the alcohol used and the selected weight ratio of COS to alcohol in the bottom. This is preferably from 0.3 to 1.7.

The vaporous mixture of alcohol and ammonia taken off at the top is, without condensing it, preferably passed under the pressure of the pressure distillation reactor to the middle region of a distillation column in which, by rectification in the bottom at at least 170° C., depending on the alcohol, selected and operating pressure, ammonia-free alcohol is produced which is recycled to the bottom of the distillation and pressure distillation reactor. At the top, ammonia is taken off in the liquid state. To prevent coating of the reflux condenser by any ammonium carbamate present, to increase the temperature at the top to at least 60° C., a corresponding proportion of alcohol is admitted. The amount of alcohol thus discharged from the circuit together with the ammonia must be replaced by fresh alcohol.

The COS/alcohol mixture produced in the bottom of the pressure distillation reactor is purified by distillation in a manner known per se, the alcohol separated off being expediently recycled to the uppermost plate of the distillation reactor.

The catalyst is added to the purified COS, before use in the cleavage, as an approximately 5% strength by weight solution or suspension in the alcohol which is also used to prepare the biscarbamate or in COS in an amount of from 5 to 400 ppm, preferably from 20 to 100 ppm. Suitable catalysts are halides or oxides of metals of groups IB, IIB, IIIB, IVB, VB, VIB, VIIB and VIIIB of the Periodic Table of the Elements. Preferable examples include chlorides of zinc or tin and oxides of zinc, manganese, iron or cobalt.

COS is preferably cleaved in a combined cleavage and rectification column in which the cleavage is carried out in the lower part and, in the upper part, the cleavage products are rectified (reactive distillation). The IOS formed is obtained as crude IOS in the side takeoff, while the pure alcohol is taken off at the top. To remove by-products formed in the cleavage, reaction mixture is discharged continuously from the bottom in an amount of from 5 to 50% by weight, preferably from 15 to 25% by weight, based on the starting amount.

The cleavage is carried out at a bottom pressure of from 5 to 100 mbar, preferably from 40 to 80 mbar, and at a bottom temperature of from 150 to 260° C., preferably from 170 to 220° C. The COS to be cleaved can alternatively be fed into the circulation to the failing-film evaporator or into the lower third of the column, preferably above the device for energy recovery.

The combined cleavage and rectification column is equipped with a falling-film evaporator for energy feed in the bottom, with a device for energy recovery in the lower third, with a device for taking off crude IOS in the upper third and with a condenser, condensate collection vessel and pump for the reflux and takeoff of pure alcohol at the top.

To avoid excessive thermal stress of the COS, the failing-film evaporator for energy feed in the bottom of the column is operated in such a manner that on a single path at most 20% by weight, preferably less than 10% by weight, of the charge is evaporated and that liquid and vapors are conducted concurrently.

Owing to the reactivity of the isocyanate groups and the silane groups, their mean residence time in the cleavage zone should be as short as possible, which is achieved by minimizing the liquid volume by appropriate structural measures and by using arranged packings having a low holdup and also by removing the IOS formed from the cleavage zone as promptly as possible by distillation. The latter is implemented by appropriate energy input in the bottom of the combined cleavage and rectification column. As a result a concentration profile is established in the column where in the bottom essentially COS, less than 3% by weight of IOS and undetectable amounts of alcohol are present, while the liquid in the lower part of the column only comprises small amounts of COS.

The reflux necessary for this is expediently generated by a condensation stage above the cleavage zone and below the IOS side takeoff. This mode of operation is particularly economical, since the energy to be removed here is produced at a relatively high temperature level and can then be utilized further, for example for heating up the starting products which are conducted into the distillation reactor for the preparation of UOS. Furthermore, this correspondingly decreases the amount of vapor, so that above this partial condenser the diameter of the column can be correspondingly decreased.

Despite the removal as promptly as possible by distillation of the IOS formed from the cleavage zone, the formation of higher-molecular-weight compounds cannot be completely prevented, so that a corresponding proportion must be continuously discharged from the bottom of the combined cleavage and rectification column. These products are conducted into a downstream reactor for reaction with the alcohol from the top of the combined cleavage and rectification column.

The crude IOS taken off from the combined cleavage and rectification column is purified in a known manner by vacuum distillation. First runnings and distillation residue are preferably recycled to the combined cleavage and rectification column. The discharge from the bottom of the combined cleavage and rectification column and the alcohol taken off there at the top are continuously mixed and, after heating to from 80 to 140° C., are reacted in a tube reactor at a pressure of 2 bar and a residence time of from 1 to 4 h, preferably 2 h, to convert the isocyanate groups to carbamate groups. The reaction product is continuously recycled to the pressure-distillation reactor onto the uppermost plate.

As will be readily appreciated by those of skill in the art, the products of this invention, carbamatoorganosilanes, ureoorganosilanes and isocyanatoorganosilanes, on account of the differently reacting functionalities, the carbamate or isocyanate groups and the silane groups, have numerous possibilities for use, for example:

for surface modification of inorganic and organic materials,
as adhesion promoters between inorganic materials and organic polymers,
as crosslinking agents for the moisture-curing of polymers,
for PU sealants,
in the coating and adhesive sector,
for the production of biologically active products, such as insecticides and herbicides.

EXAMPLES

Having generally described this invention, a further understanding can be obtained by reference to certain specific examples which are provided herein for purposes of illustration only and are not intended to be limiting unless otherwise specified.

Example 1

Preparation of ethyl N-triethoxysilylpropylcarbamate

In a 10 L distillation autoclave, 3-aminopropyltriethoxysilane (3321 g, 15 mol) are brought to reaction with urea (928 g, 15.45 mol) and ethanol (3458 g, 75 mol) at 230° C. and pressure between 35 and 23 bar. The resultant ammonia is continuously stripped out by the ethanol vapors.

After a reaction time of 9 hours, >99% of the aminoorganosilane has reacted. The main product which forms, according to GC analysis, at >90%, is ethyl N-triethoxysilylpropylcarbamate (reported without the ethanol portion). The principle by-products which form are ethyl carbamate, N-N'-di(3-triethoxy-silylpropyl)urea and 1,1,3,3,-tetraethoxy-1,3-di(ethyl N-propylcarbamate)disiloxane.

Unreacted ethanol, low-boilers and higher-molecular-weight compounds are separated off by subsequent multiple stage thin-film and short-path distillations under reduced pressure.

The colorless ethyl N-triethoxysilylpropylcarbamate then obtained has a purity of >99% (GC, SFC).

Example 2

Preparation of 3-isocyanatopropyltriethoxysilane

In a combined cleavage and rectification apparatus, ethyl N-triethoxysilylpropylcarbamate is continuously cleaved in the presence of 30 ppm of tin(II) chloride at a bottom temperature of approximately 210° C. and a bottom pressure of 75 mbar.

A portion of the bottom phase is continuously discharged from the cleavage apparatus.

The ethanol released is taken off at the top of the rectification column and recycled to the carbamate preparation as a mixture with the discharged cleavage bottom phase.

The 3-isocyanatopropyltriethoxysilane is concentrated to a purity of >99% (GC) via the side takeoff in a directly following vacuum rectification at a bottom temperature of 120° C. and a bottom pressure of 15 mbar A portion of the bottom phase of this rectification unit, where the bottom phase comprises unreacted urethane, is continuously recycled to the cleavage.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 19857532.7, filed on Dec. 14, 1998, and incorporated herein by reference in its entirety.

What is claimed is:

1. A process for preparing a carbamatoorganosilane represented by formula (V):

$$R^5O—(C=O)—NH—R^1—Si(R^2,R^3,R^4) \quad (V)$$

wherein $R^1$ is an alkylene, branched alkylene, cycloalkylene, alkenylene, alkylalkoxyalkylene, arylene, alkarylene or aralkylene group;

$R^2$, $R^3$, $R^4$ are each, independently, an alkyl, branched alkyl, cycloalkyl, alkoxy, alkoxy-substituted alkoxy, siloxy, aryl alkaryl, or aralkyl group;

$R^5$ is an alkyl, branched alkyl, cycloalkyl, aryl, alkaryl, or aralkyl group;

wherein $R^1$, $R^2$, $R^3$ and $R^4$ may each be, independently, substituted with one or more functional groups, comprising:

(a) reacting an aminoorganosilane represented by formula (I), a urea represented by formula (II) and an alcohol represented by formula (IV) in a stirred-tank cascade at 150–250° C. and 7–40 bar; or (b) reacting an aminoorganosilane represented by formula (I), a urea represented by formula (II) in an alcohol solvent represented by formula (IV) in a distillation reactor at 100–130° C. and 0.7–1.5 bar (absolute) to form an ureoorganosilane represented by formula (III), followed by (ii) reacting the ureoorganosilane represented by formula (III) with an alcohol represented by formula (IV) in a pressure distillation reactor at 150–250° C. and 7–40 bar, $$H_2N-R^1-Si(R^2,R^3,R^4) \quad (I)$$

$$H_2N-(C=O)-NH_2 \quad (II)$$

$$H_2N-(C=O)-NH-R^1-Si(R^2,R^3,R^4) \quad (III)$$

$$R^5-OH \quad (IV)$$

wherein $R^1$, $R^2$, $R^3$, $R^4$ and $R^5$ are as defined above.

2. The process of claim 1, wherein $R^1$, $R^2$, $R^3$, $R^4$ and $R^5$ each, independently, have 1 to 20 carbon atoms.

3. The process of claim 1, wherein said functional groups are selected from the group consisting of ethers, thioethers, sulfones, ketones, esters, amides and nitrites.

4. The process of claim 1, wherein $R^5$ is an alkyl, branched alkyl or cycloalkyl group.

5. The process of claim 1, which is conducted continuously.

6. The process of claim 1, which comprises (a).

7. The process of claim 1, which comprises (b).

8. A process for preparing an ureoorganosilane represented by formula (III):

$$H_2N-(C=O)-NH-R^1-Si(R^2,R^3,R^4) \quad (III)$$

wherein $R^1$ is an alkylene, branched alkylene, cycloalkylene, alkenylene, alkylalkoxyalkylene, arylene, alkarylene or aralkylene group;

$R^2$, $R^3$, $R^4$ are each, independently, an alkyl, branched alkyl, cycloalkyl, alkoxy, alkoxy-substituted alkoxy, siloxy, aryl alkaryl, or aralkyl group;

wherein $R^1$, $R^2$, $R^3$ and $R^4$ may each be, independently, substituted with one or more functional groups, comprising:

(a) reacting an aminoorganosilane represented by formula (I), a urea represented by formula (II) and an alcohol solvent represented by formula (IV) in a distillation reactor at 100–130° C. and 0.7–1.5 bar (absolute), $$H_2N-R^1-Si(^2,R^3,R^4) \quad (I)$$

$$H_2N-(C=O)-NH_2 \quad (II)$$

$$R^5-OH \quad (IV)$$

wherein $R^1$, $R,^2$, $R^3$, and $R^4$ are as defined above; and $R^5$ is an alkyl, branched alkyl, cycloalkyl, aryl, alkaryl, or aralkyl group.

9. The process of claim 8, wherein $R^1$, $R^2$, $R^3$, $R^4$ and $R^5$ each, independently, have 1 to 20 carbon atoms.

10. The process of claim 8, wherein said functional groups are selected from the group consisting of ethers, thioethers, sulfones, ketones, esters, amides and nitrites.

11. The process of claim 8, wherein $R^5$ is an alkyl, branched alkyl or cycloalkyl group.

12. The process of claim 1, which is conducted continuously.

13. A process for preparing a isocyanatoorganosilane represented by formula (VI):

$$OCN-R^1-Si(R^1,R^2,R^3,R^4) \quad (VI)$$

wherein $R^1$ is an alkylene, branched alkylene, cycloalkylene, alkenylene, alkylalkoxyalkylene, arylene, alkarylene or aralkylene group;

$R^2$, $R^3$, $R^4$ are each, independently, an alkyl, branched alkyl, cycloalkyl, alkoxy, alkoxy-substituted alkoxy, siloxy, aryl alkaryl, or aralkyl group;

wherein $R^1$, $R^2$, $R^3$ and $R^4$ may each be, independently, substituted with one or more functional groups, comprising:

(a) reacting an aminoorganosilane represented by formula (I), a urea represented by formula (II) and an alcohol represented by formula (IV) in a stirred-tank cascade at 150–250° C. and 7–40 bar; or (b) reacting an aminoorganosilane represented by formula (I), a urea represented by formula (II) in an alcohol solvent represented by formula (IV) in a distillation reactor at 100–130° C. and 0.7–1.5 bar (absolute) to form an ureoorganosilane represented by formula (III), followed by (ii) reacting the ureoorganosilane represented by formula (II) with an alcohol represented by formula (IV) in a pressure distillation reactor at 150–250° C. and 7–40 bar to produce a carbamatoorganosilane represented by formula (V);

$$R^5O-(C=O)-NH-R^1-Si(R^2,R^3,R^4) \quad (V), and$$

(c) catalytically cleaving the carbamatoorganosilane represented by formula (V) in the liquid phase, $$H_2N-R^1-Si(R^2,R^3,R^4) \quad (I)$$

$$H_2N-(C=O)-NH_2 \quad (II)$$

$$H_2N-(C=O)-NH-R^1-Si(R^2,R^3,R^4) \quad (III)$$

$$R^1-OH \quad (IV)$$

wherein $R^1$, $R^2$, $R^3$, and $R^4$ are as defined above; and $R^5$ is an alkyl, branched alkyl, cycloalkyl, aryl, alkaryl, or aralkyl group.

14. The process of claim 13, wherein $R^1$, $R^2$, $R^3$, $R^4$ and $R^5$ each, independently, have 1 to 20 carbon atoms.

15. The process of claim 13, wherein said functional groups are selected from the group consisting of ethers, thioethers, sulfones, ketones, esters, amides and nitrites.

16. The process of claim 13, wherein $R^5$ is an alkyl, branched alkyl or cycloalkyl group.

17. The process of claim 13, wherein the catalytic cleavage of (V) is conducted in a combined cleavage and rectification column.

18. The process of claim 17, wherein some of the bottom phase from the cleavage and rectification column together with the alcohol from the top of the column is recycled to (a).

19. The process of claim 13, which is conducted continuously.

20. The process of claim 13, which comprises (a).

21. The process of claim 13, which comprises (b).

* * * * *